United States Patent [19]
Castillo

[11] Patent Number: 4,911,187
[45] Date of Patent: Mar. 27, 1990

[54] DENTAL PICK BRUSH APPARATUS

[76] Inventor: David D. Castillo, 3808 S. 12th St., Phoenix, Ariz. 85040

[21] Appl. No.: 298,686

[22] Filed: Jan. 19, 1989

[51] Int. Cl.⁴ ............................................. A61C 15/00
[52] U.S. Cl. .................................. 132/321; 132/329; 15/167.1
[58] Field of Search ................ 132/321, 329; 433/141, 433/216; 15/167.1

[56] References Cited
U.S. PATENT DOCUMENTS

| | | | |
|---|---|---|---|
| 792,471 | 6/1905 | Smith | 15/187 |
| 876,185 | 1/1908 | Hillman | 15/167.1 |
| 1,784,986 | 12/1930 | Eisenberg | 132/329 |

FOREIGN PATENT DOCUMENTS

| | | | |
|---|---|---|---|
| 17666 | of 1896 | United Kingdom | 15/167.1 |
| 19504 | of 1912 | United Kingdom | 132/329 |
| WO88/01154 | 2/1988 | World Int. Prop. O. | 132/321 |

Primary Examiner—John J. Wilson
Attorney, Agent, or Firm—H. Gordon Shields

[57] ABSTRACT

Dental pick brush apparatus includes a shaft with a toothpick portion at one end and a bristle portion at the other end. The bristle portion includes a ball secured to the shaft and relatively short bristles extending outwardly from the ball in virtually all directions. The relatively short bristles, and the directions at which they extend from the ball, are particularly adapted to clean between teeth and around braces secured to the teeth, from virtually any orientation of the brush apparatus and regardless of the proximity of the braces to the teeth.

9 Claims, 1 Drawing Sheet

DENTAL PICK BRUSH APPARATUS

BACKGROUND OF THE INVENTION

1. Field of the Invention

This invention relates to dental apparatus and, more particularly, to a combination of a toothpick and a toothbrush apparatus having a toothpick portion and bristle brush portion.

2. Description of the Prior Art

U.S. Pat. No. 792,471 (Smith) discloses a toothpick with brush attachment at one end of the toothpick. The bristles of the brush are aligned with the longitudinal axis of the toothpick element.

U.S. Pat. No. 3,954,115 (Bengtsson) discloses a combination toothpick and tooth cleaning element. The apparatus discloses a toothpick portion and a roughened surface for cleaning the teeth. The apparatus is used as a dental hygiene implement for picking between teeth and for scraping tartar off teeth.

U.S. Pat. No. 4,215,478 (Thomas et al) discloses a toothpick apparatus that includes an eye, similar to a needle, at the opposite end from the pointed, pick end. String elements extend through the eye and may be pulled through the teeth. The string elements act as flossing agents, or as abrasive floss, to clean between the teeth.

U.S. Pat. No. Des. 223,651 (Hermann) discloses a design for a toothbrush. The toothbrush includes a straight handle, a pointed end, and a plurality of circular, disc-like elements adjacent to the pointed end.

It will be noted that none of the references of record disclose brush apparatus having relatively short, but circularly extending bristles, which would be particularly applicable or helpful in brushing teeth that have orthodontic elements or braces secured to them.

SUMMARY OF THE INVENTION

The invention described and claimed herein comprises a combination dental or toothpick and dental brush apparatus with a pick portion at one end of the apparatus and a brush portion at the opposite end of the apparatus. The brush portion includes relatively short bristles extending 360 degrees about the longitudinal axis of the apparatus and also extending outwardly from the end so that the bristles extend nearly completely outwardly in a ball type configuration and inwardly towards the longitudinal axis of the pick portion. Among the objects of the present invention are the following:

To provide new and useful dental pick brush apparatus;

To provide new and useful toothpick apparatus;

To provide new and useful dental brush apparatus;

To provide new and useful dental brush apparatus having bristles extending 360 degrees about a central element.

To provide new and useful toothbrush apparatus adapted particularly to brush around braces secured to teeth;

To provide new and useful dental brush apparatus having a ball secured to a stem; and To provide new and useful dental brush apparatus having a stem, a ball secured to the stem, and bristles extending outwardly from the ball in virtually all directions.

DESCRIPTION OF THE PREFERRED EMBODIMENT

Figure 1:
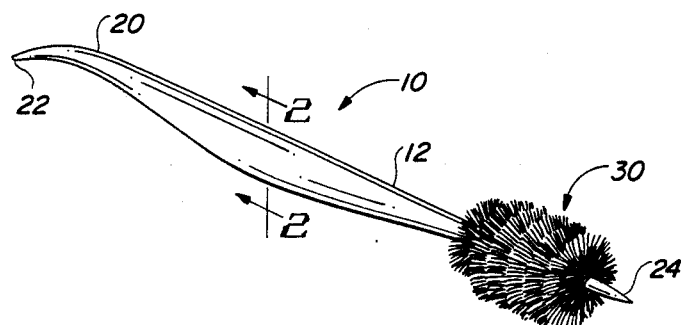
FIG. 1 is a perspective view of the apparatus of the present invention.

FIG. 1 is a perspective view of toothpick brush apparatus 10 of the present invention. The toothpick brush apparatus 10 includes a body 12 with a pick 22 at one end of the body 12 and a brush portion 30 at the opposite end of the body 12.

Figure 2:
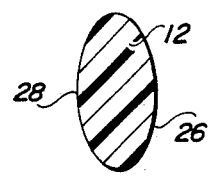
FIG. 2 is a view in partial section taken generally along line 2—2 of FIG. 1.

The body 12 has a generally oval shaped cross-sectional configuration, as best shown in FIG. 2. FIG. 2 is a view in partial section of the body 12 taken generally along line 2—2 of FIG. 1. The generally oval shaped cross-sectional configuration extends generally the full length of the body 12, or along the longitudinal axis of the body 12 between the pick 22 and the brush portion 30.

About in the center, longitudinally, of the body 12, is a thickened portion 16. The thickened portion 16 refers to the overall height of the body 12 between the pick 22 and the brush portion 30.

The generally oval shaped configuration, including the thickened portion 16, aid in the use of the apparatus by allowing a user to more easily grip the apparatus 10 than might otherwise be accomplished without the thickened portion.

The oval shape of the body 12 provides, with respect to a user, a pair of sides, including a side 26 and a side 28. the sides 26 and 28, along with the thickened portion 16, help a user control the apparatus 10 during both pick activities and brush activities.

Adjacent to the pick 22 is a curved portion 20. The body 12 curves so that the pick 22 is not directly axially aligned with the longitudinal axis of the body 12. Rather, again for convenience in manipulating the pick 22, the body includes the curved portion 20 to enhance the usage and operation of the toothpick brush apparatus 10.

Figure 5:
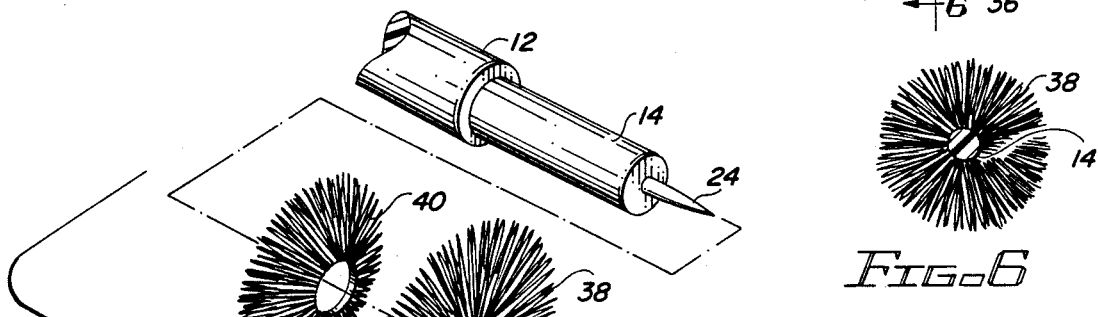
FIG. 5 is an exploded perspective view of a portion of the apparatus of the present invention.
Figure 6:
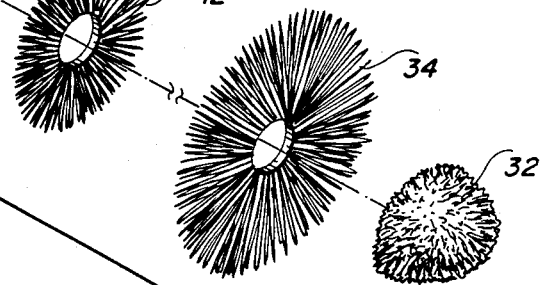
FIG. 6 is a view in partial section taken generally along line 6—6 of FIG. 4.

At the front end of the body 12, as best shown in FIG. 5, there is a reduced portion 14. The reduced portion 14 comprises a bristle pin to which the brush 30 is secured.

Figure 3:
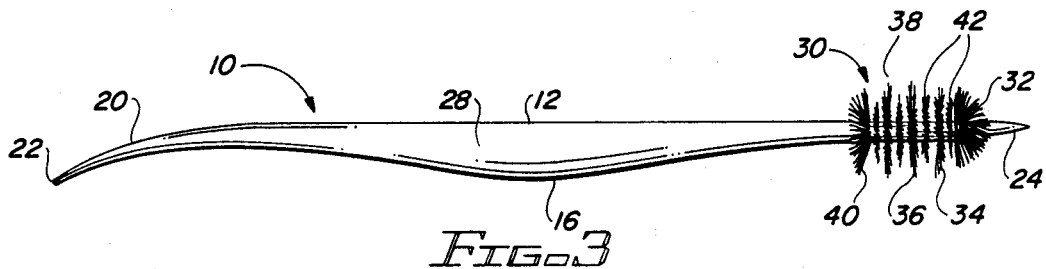
FIG. 3 is a side view of the apparatus of the present invention.
Figure 4:
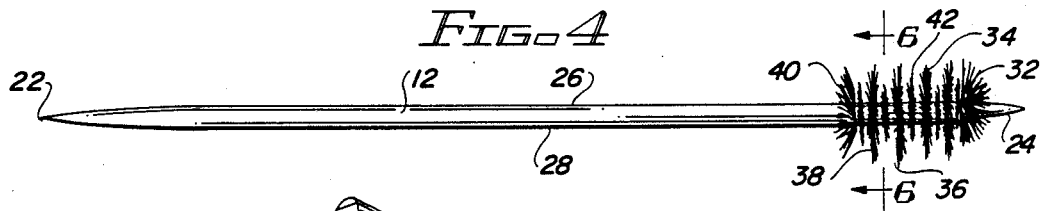
FIG. 4 is a top view of the apparatus of the present invention.

The brush 30 comprises several different elements, all of which are appropriately secured together on the pin 14. As best shown in FIGS. 3, 4, and 5, there are radially outwardly extending bristles, forwardly extending bristles, and rearwardly extending bristles. In addition, the radially outwardly extending bristles are generally of two different overall diameters, for maximizing the brushing efficiency.

The brush 30 includes a ball or tip 32 which comprises an element including generally forwardly extending bristles. In the tip element 32 the bristles extend generally forwardly, or at an acute angle to the longitudinal axis of the body 12. However, as may best be understood from FIGS. 3 and 4, the bristle elements 32 include bristles that extend not only at an acute angle, but also generally radially outwardly extending, as well. The length of the bristles of the tip or ball element 32 vary from relatively short to relatively long, particularly depending upon the angular orientation of the bristles. The forwardly extending bristles, or the bristles with the lowest or smallest acute angle, are the shortest. As the acute angle approaches the perpendicular, with respect to the longitudinal axis of the body 12, the bristles increase in length.

Rearwardly from the tip 32 are three sets of generally radially extending bristles, including a radial bristle element 34, a radial bristle element 36, and a radial bristle element 38. The radially extending bristles 34, 36, and 38 are generally spaced apart from each other along the pin 14.

Rearwardly of the bristle element 38, and spaced apart from the bristle element 38, is a rearwardly extending bristle element 40, the bristles of which are generally at an obtuse angle to the longitudinal axis of the body 12, measured from the front. Or, in other words, the bristles of the element 40 are generally at an acute angle to the longitudinal axis of the body 12 if measured from the rear, rather than from the front. At any rate, the rearward bristle element 40 includes individual bristles which, like the bristle element 32, include bristles extending at various angles to the longitudinal axis of the body 12 up to generally radially extending bristles.

Obviously, the element 40 could not include bristles extending generally directly rearwardly due to the body 12. However, the bristles extend generally rearwardly and vary in length as the angle of the bristles varies up to a maximum bristle length of the bristles which extend generally radially outwardly from the longitudinal axis of the body 12.

Between the bristle elements 32, 34, 36, 38, and 40, are a plurality of intermediate radial bristles 42. The length of the intermediate radial bristle elements 42 is generally less than that of the radially extending bristle elements, as discussed above. The intermediate radial bristle elements comprise additional bristle elements to aid in removing foreign material and in cleaning the teeth of a user.

The rearwardly extending bristles 40, as well as the forwardly extending bristles 32, are of particular use in cleaning orthodontic elements, such as wire braces, on a user's teeth. The forwardly and rearwardly extending bristles, as well as the generally radially extending bristles, allow a user to conveniently and expeditiously have access to all areas of the teeth, and all areas of orthodontic elements or appliances secured to the teeth, for cleaning purposes. As is well known and understood, orthodontic elements come in various forms, and the cleaning of the appliances, as secured to teeth, can be extremely frustrating with conventional toothbrushes. The apparatus of the present invention overcomes the problems of "ordinary" toothbrushes by providing bristles which extend in different directions so as to enable a user to clean the appliances and the teeth, on the inside and the outside of the teeth and on the top and bottom teeth.

Extending outwardly from the tip 32, and from the forwardly extending bristles that are included in the top 32, is a pick 24. the pick 24 extends only a relatively a short distance outwardly from the bristle elements 32. The pick 24 is axially aligned with the longitudinal axis of the body 12, and is secured to the pin 14, as best shown in FIG. 5.

The inclusion of two pick elements, the pick element 22 which extends outwardly from the curved portion 20 of the body 12, and the straight pick 24, which extends axially outwardly from the pin 14 and the body 12, provides dual pick elements for the apparatus, one of which is curved and one of which is straight. The inclusion or utilization of the two picks allows greater flexibility for a user in picking foreign material from a user's teeth and also from orthodontic appliances.

The brushes 30, or the bristle elements which comprise the brush 30, are preferably relatively soft so as to not do damage to gum tissue or to orthodontic appliances. Moreover, the utilization of relatively soft brushes helps to prevent gingivitis and other irritations on the gums and in the mouth.

The pick brush apparatus 10 is designed to be disposable, or to be used only once and then disposed of. The employment of such an apparatus accordingly allows a user to conveniently carry the apparatus in a shirt pocket, coat pocket, a purse, etc. If desired, a brush 30 may include fluoridated elements, scented elements, etc. Breath fresheners of various scents may be included, as desired.

The body 12 may be made of any appropriate material, preferably a type of plastic. The bristles of the brush 30 may also be made of any appropriate material, such as nylon, or the like.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Dental pick brush apparatus, comprising, in combination:
   body means for enabling a user to grasp and use the apparatus, and having a longitudinal axis and a first end and a second end;
   first pick means at the first end of the body means for picking foreign material from a user's tooth;
   brush means at the second end of the body means for brushing a user's teeth, including first bristles extending radially outwardly, substantially perpendicularly to the longitudinal axis of the body means, and second bristles extending forwardly along the longitudinal axis of the body means; and
   second pick means extending through the second bristles generally along the longitudinal axis of the body means for picking foreign material from the users's teeth.

2. The apparatus from claim 1 in which the body means includes a curved portion adjacent to the first pick means.

3. The apparatus of claim 1 in which the brush means includes rows of bristles extending outwardly from the body means.

4. The apparatus of claim 3 in which the second pick means extends outwardly from the rows of bristles generally along the longitudinal axis of the body means.

5. The apparatus of claim 1 in which the second bristles of the brush means extend generally forwardly along the longitudinal axis of the body means and at acute angles thereto for brushing a user's teeth and for brushing orthodontic elements on a user's teeth.

6. The apparatus of claim 1 in which the brush means further includes third bristles extending generally rearwardly along the longitudinal axis of the body means at obtuse angles thereto for brushing a user's teeth and for brushing orthodontic elements on a user's teeth.

7. The apparatus of claim 1 in which the brush means includes first radial bristles comprising a plurality of spaced apart first bristle elements generally having a first length.

8. The apparatus of claim 7 in which the brush means includes second radial bristles comprising bristles disposed between the plurality of spaced apart first bristle elements and generally having a second length, which second length is less than the first length of the first bristle elements.

9. The apparatus of claim 8 in which the second radial bristles includes a plurality of second bristle elements disposed between the plurality of first bristle elements.

* * * * *